United States Patent [19]

Mont

[11] 4,059,690

[45] Nov. 22, 1977

[54] TOPICAL LIQUID OR OINTMENT

[76] Inventor: Walter Mont, 8655 N. Miami, Miami, Fla. 33150

[21] Appl. No.: 764,850

[22] Filed: Feb. 2, 1977

[51] Int. Cl.² .................. A61K 31/60; A61K 31/045; A61K 33/18
[52] U.S. Cl. .................. 424/150; 424/231; 424/343
[58] Field of Search .................. 424/45, 150, 230, 231, 424/343

[56] References Cited

U.S. PATENT DOCUMENTS

| | | | |
|---|---|---|---|
| 2,105,197 | 1/1938 | McCrea | 424/231 |
| 3,081,232 | 3/1963 | Powers et al. | 424/45 |
| 3,751,565 | 8/1973 | Santorelli | 424/231 |

OTHER PUBLICATIONS

Chem. Abst. – 42-2731 G (1948).
Chem. Abst. – 53-17421e (1957).
Martindale, The Extra Pharmacopoeia, vol. 1, 24th Ed., pp. 875–880 (1958).

*Primary Examiner*—Stanley J. Friedman

[57] ABSTRACT

A liquid ointment for topical application to relieve arthritic pain. The liquid is composed of 90 parts by volume of tincture of iodides and 10 parts by volume of menthol crystals liquefied in the tincture of iodides and thoroughly mixed with 1 to 1½ parts by volume of salicyclic acid and 1½ parts by volume of menthyl salicylate. The liquid is topically applied and worked into the skin preferably using a massage type vibrator. The liquid may be combined as preferred in a range of concentrations with a non-greasy base for use as an ointment for topical application.

2 Claims, No Drawings

TOPICAL LIQUID OR OINTMENT

FIELD OF THE INVENTION

This invention relates to an ointment and more particularly to a liquid for topical application and which may be combined in a non-greasy base as an ointment for relieving arthritic pain and bursitis; and which is applied by a massage type vibrator.

BACKGROUND OF THE INVENTION

In the past there have been numerous types of topical application which have sought to relieve the pain of arthritis and bursitis. This invention is of such an ointment. Relevant prior art is that found in U.S. Letters Pat. No. 2,666,573, a medical compound for rheumatism; U.S. Letters Pat. No. 97,714, an improved compound for treating rheumatism; U.S. Letters Pat. No. 41,883, a topical medicine; and U.S. Letters Pat. No. 3,081,232, an iodine preparation and method of disinfecting the skin.

OBJECTS OF THE PRESENT INVENTION

It is an object of this invention to provide an improved liquid for topical application applied with a massage type vibrator or which liquid may be combined with a non-greasy base to form a topically applied ointment. The liquid is composed of about 90 parts of tincture of iodides and 10 parts of menthol crystals liquefied in the tincture of iodides and wherein there is mixed 1 to 1½ parts of salicylic acid and 1½ parts of menthyl salicylate which are thoroughly mixed and applied to the skin by massaging it and working it in using a strong massage type vibrator.

DESCRIPTION OF PREFERRED EMBODIMENT

The present invention is of a liquid, which may be combined with a base to form an ointment. In either case it is to be applied topically. Preferably it is to be worked into the skin using a strong massage type vibrator apparatus. Preferably the liquid consists of 90 parts by volume of tincture of iodides and 10 parts by volume of menthol crystals which are liquefied in the tincture of iodides. There is added to the aforesaid, 1 to 1½ parts of salicylic acid and 1½ parts of menthyl salicylate and the aforementioned parts by volume are thoroughly mixed and, later, massaged into the skin using a strong massage type vibrator apparatus, preferably as strong as can be utilized on the particular surface where rheumatism or arthritis is bothering the user.

The benefit appears to result from the application which is applied in the manner described; and tends to relieve arthritic pain and bursitis.

Example, a suitable liquid to be topically applied may be prepared utilizing 90 parts of tincture of iodides and 10 parts of menthol crystals liquefied in the tincture of iodides and adding 1 to 1½ parts of salicylic acid and 1½ parts of menthyl salicylate, the parts referred to above being by volume. Upon thorough mixing, the same may be applied topically to the skin and, preferably, worked into it using a strong massage type vibrator as is possible on a particular location of the body to which it is applied. Additionally, the liquid may be mixed in a ratio of one part of the liquid mixture to 7 to 10 parts, (preferably 8), of a base of any suitable selection. This results in an ointment which may be applied topically.

What is claimed is:

1. A liquid to be applied topically comprising 90 parts by volume of tincture of iodides, 10 parts of menthol crystals liquefied in the tincture of iodides and 1 to 1½ parts of salicylic acid and 1½ parts of menthyl salicylate, said ingredients being thoroughly mixed to be topically applied.

2. The ointment as set forth in claim 1 wherein the liquid as defined and claimed is mixed with a non-greasy base in the range of about 10 parts of the liquid to 90 parts of the non-greasy base.